(12) United States Patent
Sarrazin et al.

(10) Patent No.: US 8,302,477 B2
(45) Date of Patent: Nov. 6, 2012

(54) BALANCED MECHANICAL RESONATOR FOR POWDER HANDLING DEVICE

(75) Inventors: Philippe C. Sarrazin, Palo Alto, CA (US); Will M. Brunner, Mountain View, CA (US)

(73) Assignee: Olympus NDT, Waltham, MA (US)

( * ) Notice: Subject to any disclaimer, the term of this patent is extended or adjusted under 35 U.S.C. 154(b) by 732 days.

(21) Appl. No.: 12/378,032

(22) Filed: Feb. 9, 2009

(65) Prior Publication Data

US 2009/0235747 A1    Sep. 24, 2009

Related U.S. Application Data

(60) Provisional application No. 61/065,216, filed on Feb. 8, 2008.

(51) Int. Cl.
*G01H 13/00* (2006.01)
*B01L 3/00* (2006.01)
(52) U.S. Cl. ........................ 73/579; 73/864.91
(58) Field of Classification Search .................. 73/579
See application file for complete search history.

(56) References Cited

U.S. PATENT DOCUMENTS 6,974,362 B2 * 12/2005 Lindell et al. ................. 451/5
7,113,265 B1 * 9/2006 Sarrazin et al. ............... 356/73

* cited by examiner

*Primary Examiner* — Hezron E Williams
*Assistant Examiner* — Gregory J Redmann
(74) *Attorney, Agent, or Firm* — Ostrolenk Faber LLP

(57) ABSTRACT

A system incorporating a balanced mechanical resonator and a method for vibration of a sample composed of granular material to generate motion of a powder sample inside the sample holder for obtaining improved analysis statistics, without imparting vibration to the sample holder support.

14 Claims, 3 Drawing Sheets

BALANCED MECHANICAL RESONATOR FOR POWDER HANDLING DEVICE

CROSS-REFERENCE TO RELATED PATENT APPLICATION

This application relates to U.S. Provisional Patent Application No. 61/065,216 filed on Feb. 8, 2008, entitled BALANCED MECHANICAL RESONATOR FOR POWDER HANDLING DEVICE, which is hereby incorporated herein in its entirety by this reference.

STATEMENT REGARDING FEDERALLY SPONSORED RESEARCH

The United States Government has certain rights to the subject matter of this invention pursuant to NASA contract number NNA06CQ54C.

BACKGROUND OF THE INVENTION

1. Field of the Invention

The present invention relates generally to powder handling devices and, more particularly, to a powder handling device that comprises a mechanism to vibrate a powder sample holder during analysis in an analytical instrument. Specifically, one embodiment of the present invention provides a system incorporating a balanced mechanical resonator and a method for vibration of a sample composed of granular material to generate motion of the powder sample inside the sample holder for obtaining improved statistics of analysis in an analytical instrument, without imparting vibration to the sample holder support.

2. Description of the Prior Art

Various devices for handling powder samples in analytical instruments are known. One known device is disclosed in U.S. Pat. No. 7,113,265 (Powder handling device for analytical instruments).

When using a known non-balanced mechanical vibrator (i.e., a vibrator not fitted with a balancing mass to compensate the inertial forces of the primary mass), the inertial forces produced by the vibration are transmitted to the chassis of the sample holder of the powder handling device through the mounting links. This can result in vibration of other components even far away from the vibrator. Vibration energy is then wasted in these parasite vibrations, and the resulting amplitude of vibration of the primary resonator is diminished.

It would be desirable to provide a solution that overcomes the disadvantages of known powder handling devices. More particularly, it would be desirable to provide a mechanism that substantially eliminates vibrations transmitted to the chassis of the sample holder. It would also be desirable to reduce parasitic vibrations that reduce the amplitude of vibrations applied to the powder sample being analyzed.

SUMMARY OF THE INVENTION

One embodiment of the present invention provides a system and method for vibrating a sample composed of granular material to generate motion of the powder sample inside the sample holder without transfer of the vibrations to the structure to which the sample holder is mounted. The system and method in accordance with the present invention provide improved analysis statistics of a powder sample in an analytical instrument.

In accordance with a preferred embodiment of the present invention a balanced resonator is provided for a powder handling device. The system and method in accordance with the present invention substantially eliminate the amount of vibration transmitted to the chassis of the sample holder so that unwanted vibration of the structure that mounts the sample holder is dramatically reduced compared to a non-balanced vibrator structure (i.e., a vibrator not fitted with a balancing mass to compensate the inertial forces of the primary mass). The vibration is decoupled from other mechanical components of the system, making the vibration more stable and less sensitive to the manner in which the device is mounted in an analytical instrument.

Preferably, in accordance with one embodiment of the system and method of the present invention, the vibrator is designed for operation at resonance. Consequently, the system and method in accordance with the present invention obtain large amplitudes of vibration with minimal actuator force.

In accordance with a preferred embodiment of the system and method of the present invention, mechanical amplification is provided. This allows obtaining vibration amplitudes far greater than that of the actuator.

Also, in accordance with the system and method of the present invention, the noise level emitted by the system is reduced when the sample is vibrated.

The foregoing and other objects, features, and advantages of the present invention will become more readily apparent from the following detailed description of various embodiments, which proceeds with reference to the accompanying drawing.

BRIEF DESCRIPTION OF THE DRAWING

The various embodiments of the present invention will be described in conjunction with the accompanying figures of the drawing to facilitate an understanding of the present invention. In the figures, like reference numerals refer to like elements. In the drawing.

DETAILED DESCRIPTION OF THE PREFERRED EMBODIMENTS

Figure 1:
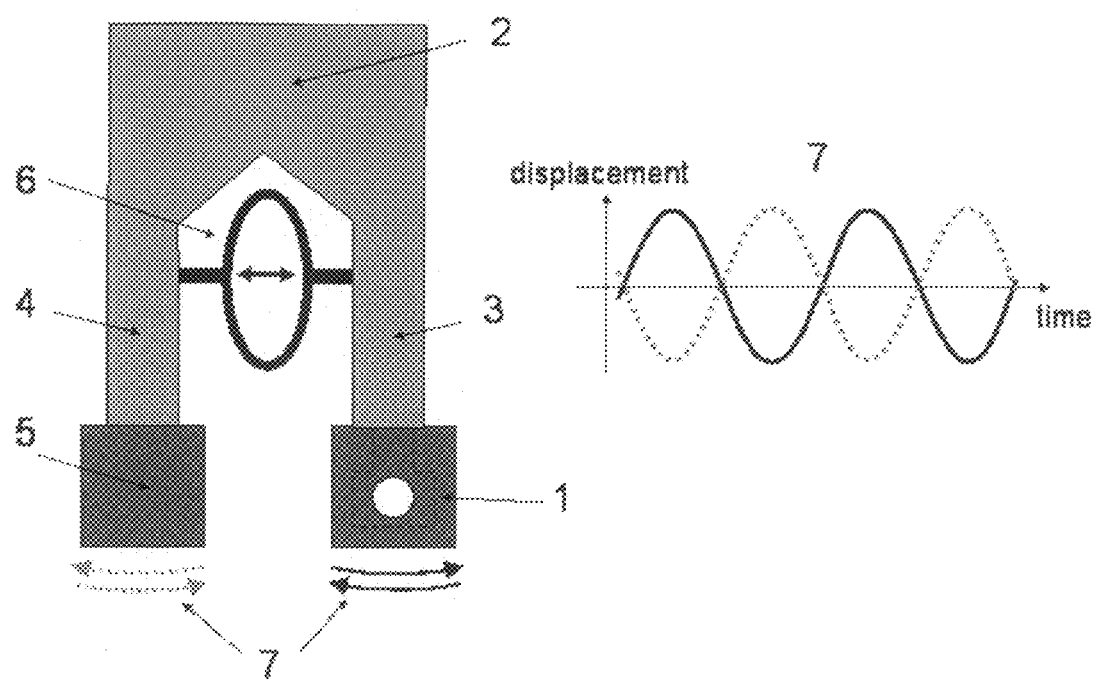
FIG. 1 is a block diagram illustrating one embodiment of the system in accordance with the present invention comprising a balanced resonator for a powder handling device.

Referring to the drawing figures, FIG. 1 shows a balanced resonator for a powder handling device. A sample holder 1 contains granular material to be analyzed by an analytical instrument. When the analytical instrument uses X-rays, the sample holder 1 is fitted with one or several X-ray windows through which the analyses are performed.

The sample holder 1 is attached to a sample holder arm 3 of a balanced mechanical resonator 2. A balancer arm 4 is fitted with a counterweight mass 5. An actuator 6 excites the resonator 2 at or near one of its resonance frequencies to obtain vibration in anti-phase, as indicated by the numeral 7.

The structure of the actuator 6 may be piezoelectric, electromagnetic, pneumatic, or the like. For example, the actuator 6 may be an APA60S actuator available from Cedrat located in Grenoble, France. In the embodiment such as shown in FIG. 1, the system benefits from a mechanical amplification, allowing vibration at higher amplitude than the actuator stroke. The mechanical resonator 2 is preferably designed to have a resonance frequency best suited to the sample motion (typically, 1-3 kHz).

Figure 2:
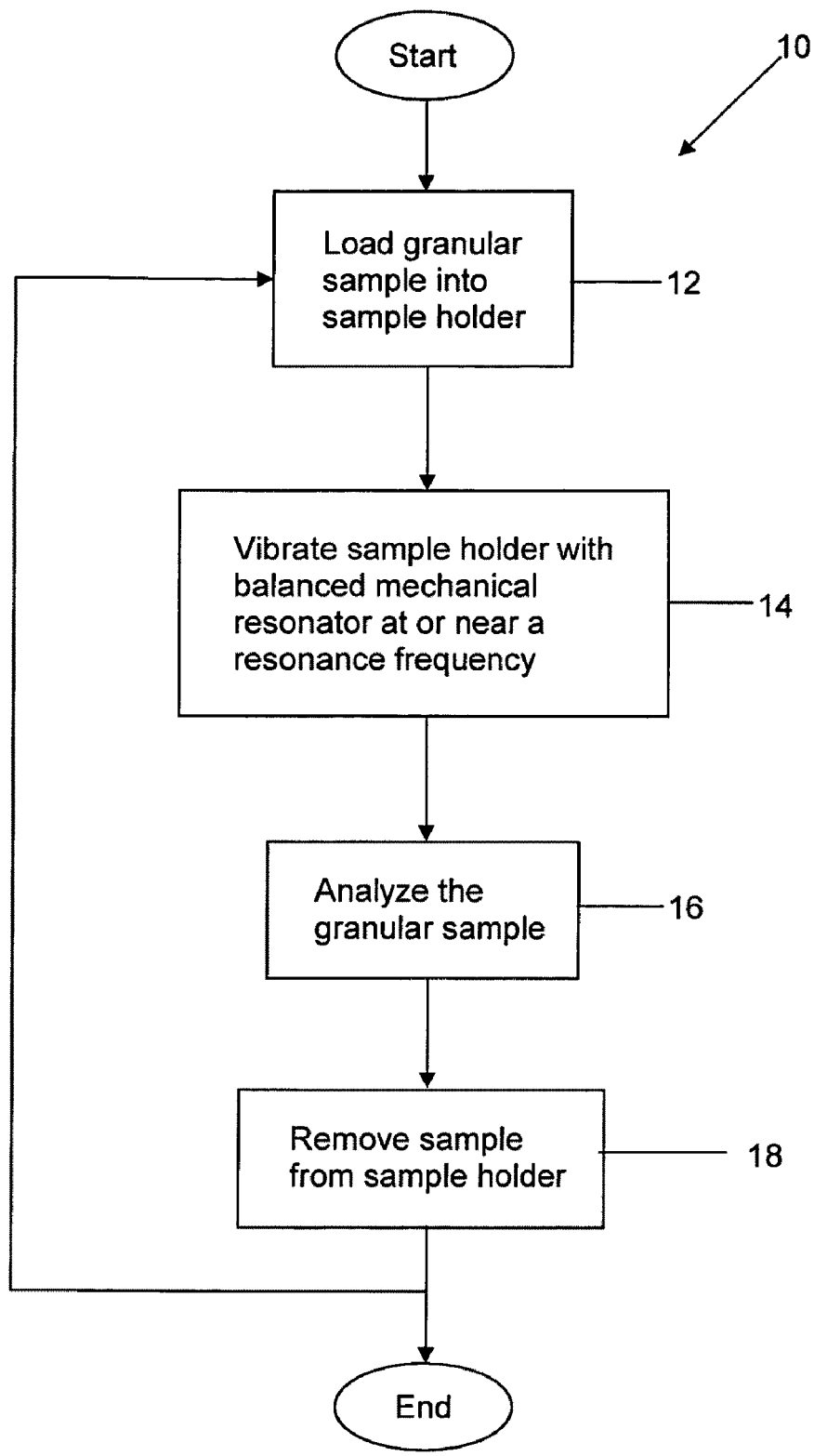
FIG. 2 is a flow diagram illustrating a method in accordance with one embodiment of the present invention.

A preferred embodiment of the method in accordance with the present invention is shown in FIG. 2, generally indicated by the numeral 10. A user loads the granular sample into the sample holder 1, as indicated by a step 12 shown in FIG. 2. During analysis in the instrument, the sample holder 1 is vibrated by the balanced mechanical resonator 2 at sufficient amplitude to obtain granular convection of the sample, as indicated by a step 14 shown in FIG. 2. This is typically obtained when vibrating the system at or near a resonance frequency of the balanced mechanical resonator 2. The mechanical excitation is produced by the actuator 6. The configuration is such that the counterweight mass 5 vibrates in anti-phase with the sample holder 1, allowing cancellation of primary order inertial effects. This structure produces a sharp mechanical resonance that allows achieving high vibration amplitude with minimal force input from the actuator 6. The balanced structure of the vibrator limits the amount of vibration transmitted to the chassis through the mechanical assembly holding the vibrator. The granular sample is then analyzed, as indicated by a step 16 shown in FIG. 2. After analysis of the granular sample, the sample is removed from the sample holder 1, as indicated by a step 18 shown in FIG. 2. Subsequently, another sample may be loaded into the sample holder 1 and analyzed, as indicated by the arrow from step 18 to step 12 shown in FIG. 2.

Figure 3:
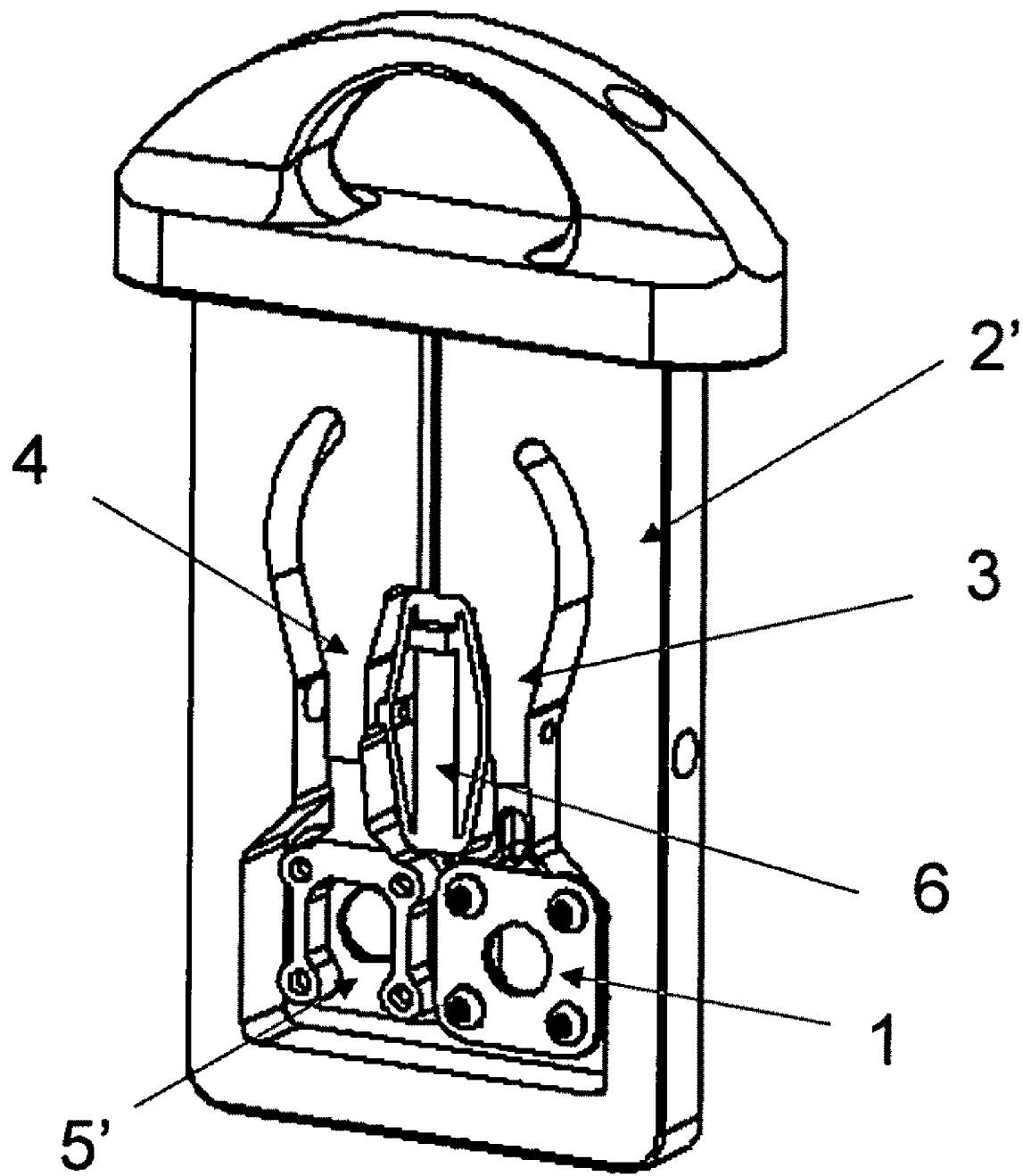
FIG. 3 is an isometric view of an alternative embodiment of the system in accordance with the present invention comprising a balanced resonator for a powder handling device.

In accordance with one contemplated alternative preferred embodiment shown in FIG. 3, a balanced resonator 2' comprises two sample holders 1 and 5', in which one sample holder 5' acts as the counterweight mass. In this embodiment, the sample holders 1 and 5' balance each other.

In accordance with another contemplated alternative embodiment, a non-symmetric resonator structure is provided, in which a counterweight of substantially different mass than the sample holder vibrates at a different amplitude than the sample holder such that the inertial effects on both sides substantially cancel each other.

In accordance with yet another contemplated alternative embodiment, the mechanical resonator may have more than one counterweight mass balancing one or several sample holders.

In accordance with a further contemplated alternative embodiment, the sample holder and/or the counterweight mass is (are) suspended with multiple links/arms instead of the single arm structure shown in FIGS. 1 and 3.

In accordance with yet another contemplated alternative embodiment, an actuator is provided, that can transmit an oscillating or pulsed force to the resonator with no direct permanent contact with the resonator.

While the foregoing description has been with reference to particular embodiments and contemplated alternative embodiments of the present invention, it will be appreciated by those skilled in the art that changes in these embodiments may be made without departing from the principles and spirit of the invention. Accordingly, the scope of the present invention can only be ascertained with reference to the appended claims.

What is claimed is:

1. A balanced resonator for a powder handling device for granular material to be analyzed by an analytical instrument, comprising:
    a sample holder adapted to hold the granular material to be analyzed;
    a balanced mechanical resonator mountable to an external chassis, comprising a) a sample holder arm attached to the sample holder in which the granular material is loaded and b) a balancer arm fitted with a counterweight mass; and
    an actuator to excite the resonator at or near one of its resonance frequencies to obtain vibration of the sample holder arm and balancer arm with respect to each other by imparting angular motion less than 360 degrees in anti-phase, the actuator producing a given excitation force to obtain convection of granular material loaded in the sample holder;
    wherein a mechanical amplification is produced to enable vibration at a higher amplitude than the actuator excitation force;
    whereby vibrations transmitted to the external chassis are substantially eliminated.

2. The balanced resonator of claim 1, further comprising an analytical instrument that emits X-rays, wherein the sample holder is fitted with one or more X-ray windows through which analyses are performed.

3. The balanced resonator of claim 1 wherein the actuator comprises one of a piezoelectric, electromagnetic, or pneumatic device.

4. The balanced resonator of claim 1 wherein the resonance frequency is in the range of approximately 1-3 kHz.

5. The balanced resonator of claim 1 wherein the counterweight mass comprises another sample holder.

6. A method for vibrating a sample in a powder handling device for granular material to be analyzed by an analytical instrument, comprising the steps of:
    loading the granular material into a sample holder;
    vibrating the sample holder with a balanced mechanical resonator at sufficient amplitude to obtain granular convection of the granular material loaded in the sample holder, such that a counterweight mass of the balanced mechanical resonator and the sample holder are in angular motion less than 360 degrees with respect to each other and the counterweight mass vibrates in anti-phase with the sample holder, thereby allowing cancellation of primary order inertial effects.

7. The method of claim 6 wherein the step of vibrating the sample holder with a balanced mechanical resonator at sufficient amplitude to obtain granular convection of the granular material comprises vibrating the sample holder at or near a resonance frequency of the balanced mechanical resonator.

8. The method of claim 6, further comprising the step of analyzing the granular material.

9. The balanced resonator of claim 1 wherein a counterweight of substantially different mass than the sample holder vibrates at a different amplitude than the sample holder such that inertial effects substantially cancel each other.

10. The balanced resonator of claim 1, further comprising at least a second counterweight mass fitted to the balancer arm.

11. The balanced resonator of claim 5, further comprising at least a second counterweight mass fitted to the balancer arm.

12. The balanced resonator of claim 1, further comprising at least a second sample holder attached to the sample holder arm.

13. The balanced resonator of claim 10, further comprising at least a second sample holder attached to the sample holder arm.

14. The balanced resonator of claim 1 wherein the actuator produces an oscillating or pulsed excitation force without direct permanent contact with the resonator.

* * * * *